United States Patent [19]

Arnaud et al.

[11] 4,407,801

[45] Oct. 4, 1983

[54] ANTI-ISCHEMIC PHARMACEUTIC COMPOSITIONS

[75] Inventors: Jean-Claude Arnaud, La Garenne Colombes; Michelle Devissaguet, Neuilly-sur-Seine, both of France

[73] Assignee: Science Union Et Cie, Suresnes, France

[21] Appl. No.: 306,224

[22] Filed: Sep. 28, 1981

[30] Foreign Application Priority Data

Sep. 30, 1980 [FR] France .............................. 80 20919

[51] Int. Cl.$^3$ .................... A61K 31/495; A61K 31/70
[52] U.S. Cl. ..................................... 424/250; 424/180
[58] Field of Search ................................. 424/180, 250

[56] References Cited

U.S. PATENT DOCUMENTS 3,262,852  7/1966  Servier ................................ 424/250

OTHER PUBLICATIONS

Mehrotra, T. et al., *Brit. J. Clin. Pract.*, 21(11), 553 (1967).

Brodbin, P. et al., *Brit. J. Clin. Pract.*, 22(9), 395 (1968).
Saito, D., *Japan Circ. J.*, 40, 363, (1976).

*Primary Examiner*—Richard A. Schwartz
*Attorney, Agent, or Firm*—Gordon W. Hueschen

[57] ABSTRACT

The subject of the invention is a novel pharmaceutical composition, especially having an anti-ischaemic action, containing, in combination, a high dosage (within the range of from 20 to 80 mg) of the dihydrochloride (or another mineral or organic salt) of 1-(2,3,4-trimethoxybenzyl)piperazine and a disintegrating agent, such as mannitol or sodium carboxymethyl starch, that has the effect of liberating the salt of 1-(2,3,4-trimethoxybenzyl)piperazine virtually instantaneously in the organism, this composition being, furthermore, advantageously enclosed in a thin coating film or held together by a binder that is itself readily disintegrated in situ in the organism in such a manner that it makes possible a "flash" action, that is to say a virtually instantaneous action, of the above-mentioned salt in situ. This composition is administered to the patient at a dosage of from 20 to 80 mg/day.

6 Claims, No Drawings

ANTI-ISCHEMIC PHARMACEUTIC COMPOSITIONS

This invention relates to a method for treating ischaemia.

PRIOR ART

U.S. Pat. No. 3,262,852 described a novel vasodilative substance constituted by the dihydrochloride of 1-(2,3,4-trimethoxybenzyl)piperazine of the formula

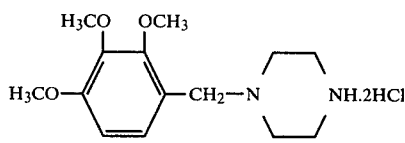

named trimetazidine dihyrochloride.

The corresponding medicament is "VASTAREL" (registered mark) listed in the "Dictionnaire Vidal". (O.V.P. Paris, France).

The above-cited patent and the Dictionnaire Vidal provide for the use of trimetazidine dihydrochloride at the following dosages.
(a) The patent:
from 0.25 to 0.5 mg/kg, producing an increase in the femoral blood flow, without varying the general arterial blood pressure (in the dog),
from 1 to 2 mg/kg, producing a fall in the general arterial blood pressure (in the dog and cat);
(b) Vidal:
from 2 to 4 tablets (of 3 mg)/day, that is to say from 6 to 12 mg/day.

The Applicants have now found that a composition containing, in combination, from 20 to 80 mg of the dihydrochloride (or another mineral or organic salt) of 1-(2,3,4-trimethoxybenzyl)piperazine and a disintegrating agent, such as mannitol or sodium carboxymethyl starch, that has the effect of liberating the salt of 1-(2,3,4-trimethoxybenzyl)piperazine virtually instantaneously in the organism, this composition being, furthermore, advantageously enclosed in a thin coating film or held together by a binder, itself readily disintegrated in situ in the organism in such a manner that it makes possible a "flash" action, that is to say a virtually instantaneous action, of the above-mentioned salt in situ, constitutes a pharmaceutical composition having an anti-ischaemic action.

Amongst the addition salts, there may be mentioned more especially the salts with a mineral acid, such as the hydrochloride, or the phosphate, or with an organic acid, such as the acetate, lactate, pyruvate, tartrate, citrate, maleate, fumarate, benzoate, 2,4-dichlorobenzoate, nicotinate, isonicotinate, benzenesulphonate, naphthalenesulphonate, p-toluenesulphonate, thiazole 5-carboxylate, methanesulphonate, ethanesulphonate, isethionate, glucose 1-phosphate or the glucose 1,6-diphosphate.

As 1-(trimethoxybenzyl)piperazine is a dibasic compound, the addition salt is generally formed with two equivalents of a monovalent acid. It is, however, possible to form a salt with a single equivalent of a monovalent acid.

Amongst all the possible salts, the dihydrochloride is mentioned more especially as the active principle of the pharmaceutical compositions according to the invention.

According to the above-cited patent and the Dictionnaire Vidal (article on Vastarel), it was indicated that trimetazidine hydrochloride, at dosages of from 6 to 12 mg daily, produced a vasodilative action owing to adrenolytic or noradrenolytic effects. This resulted in an action, having a peripheral origin, on the vessels of the general circulatory system, especially on the coronary vessels. These compositions were therefore directed at patients suffering from arteritis, coronaritis, Raynaud's disease, nocturnal acroparasthesia or functional disorders of the veins. The compositions used were sugar-coated tablets that dissolved slowly and contained 1% of active principle associated with scarcely soluble excipients.

It has now been found, and this constitutes the subject of the present invention, that, at considerably higher dosages and in association with a disintegrating agent that ensures a very rapid action, the peripheral vasodilative effect no longer occurs and the blood flows or the effects on blood pressure found with low dosages are stabilised or virtually eliminated. In contrast, at dosages of active principle within the range of from 20 to 80 mg/day, that is to say up to ten times stronger than those previously described, novel effects appear that are suitable for the treatment of different diseases. This composition therefore constitutes a novel medicament for the treatment of the metabolic effects of ischaemia.

Amongst the excipients that are suitable for accelerating the action by bringing about the above-mentioned "flash" effect, there may be mentioned starches, chemically modified starches and mannitol.

As excipients or inert vehicles for oral, parenteral or rectal use, there may be mentioned, for the solid oral forms, calcium carbonate, tricalcium phosphate, magnesium phosphate, mixed silicates of magnesium, silica, titanium silicate, talc and magnesium stearate; for the liquid forms for drinking or injecting, water, sugar solutions, gum solutions and saline solutions; and for suppositories, cocoa butter or polyethylene glycol stearates.

It was also found that galenic compositions having accelerated dissolution reinforced the effectiveness of that protective effect against the metabolic disorders caused by hypoxia; that effect was unexpected since metabolic disorders develop over several hours or even several days and the composition showed itself more active with a dissolution beginning from one to two minutes after ingestion.

It is revealed in the literature that ischaemia is a reduction in the blood flow at the tissue level and constitutes a serious occurrence because of its local metabolic consequences massive use of the glucidic substrates which surge into the metabolic block of the lactates, which results in acidosis;

breakdown of the energy activity of the cell, shown by a fall in the intracellular level of adenosine triphosphoric acid, even when there is still a supply of oxygen;

paralysis of the cellular energy-consuming functions and deceleration, then arrest, of the ionic pumps of the membrane with the following consequences:
  loss of intracellular potassium;
  massive influx of sodium and water causing oedema of the cell;
  diminution in the electrical polarity of the membrane.

The long-term consequence is the death of the cell.

The compositions according to the invention restore the energy activity of the cell exposed to ischaemia, maintain an intracellular level of adenosine triphosphoric acid comparable to that of the cell when functioning normally, permit the ionic pump of the membrane to function well and preserve the cross-membrane gradients of sodium and potassium. This maintenance of the cell homeostasis is shown at the haemodynamic level by a reduction in the work of the ischaemic myocardium.

The compositions according to the invention therefore find use in:

cardiology, in the treatment of chronic angina pectoris, ophthalmology, in the treatment of chorio-retinal disorders of ischaemic origin (angiosclerosis, retinal ischaemia, degeneration of the macula), otology, in the treatment of cochleovestibular disorders (vertigo, Ménière's disease, tinnitus).

In a preferred mode, the pharmaceutical compositions according to the invention contain 20 or 40 mg of the addition salt of 1-(2,3,4-trimethoxybenzyl)piperazine together with an excipient or an inert vehicle.

Especially, there are preferably used compounds containing 20 mg of the active principle or drops for drinking containing 20 mg of active principle per ml.

The composition is made in the form of film-coated tablets having a water-soluble coating that is approximately 1/10 mm thick, the active principle being concentrated to 20%. Amongst the rapidly soluble excipients there may be mentioned mannitol.

The daily dosage is within the range of from 20 to 80 mg of active principle, divided into from 1 to 3 equal administrations.

The following Examples illustrate the invention without limiting it in any way.

EXAMPLE 1

| | |
|---|---|
| trimetazidine dihydrochloride | 0.020 g |
| corn starch | 0.026 g |
| mannitol | 0.034 g |
| polyvidone excipient | 0.004 g |
| magnesium stearate | 0.001 g |
| talc | 0.005 g |
| coating film | 0.005 g |

The coating film is very fine and the whole constitutes a small tablet.

The presence of mannitol, the use of a very fine coating film and the manufacture of a small tablet ensures that the composition according to Example 1 has an immediate action having a metabolic effect.

The dissolution time of the active principle is from 2 to 7 minutes for a dissolution of 50%, and from 15 minutes for a rate of dissolution greater than 95%.

EXAMPLE 2

| | |
|---|---|
| trimetazidine dihydrochloride | 0.020 g |
| colloidal silica (compression effect) | 0.011 g |
| stearic acid (anti-adherent) | 0.0036 g |
| carboxymethyl starch (rapid disintegrating agent) | 0.012 g |
| microcrystalline cellulose (binder) | 0.1335 |
| lactose (ease of filling) | 0.148 |
| magnesium stearate (lubricant) | 0.0018 |

The sodium carboxymethyl starch added to the trimetazidine dihydrochloride permits a rapid disintegration of this latter constituent of the composition of Example 2: the disintegration time is from one minute; there is a physical "explosion" of the compound.

The other products serve to facilitate the formation into tablets in the press bringing about the direct compression.

The pharmacological studies carried out with the novel compositions according to the invention, especially with the compositions according to the above-mentioned Examples 1 and 2, and the results of the clinical experiments using these compositions will now be discussed.

(A) Pharmacological studies carried out using the compositions according to the invention The compositions according to the invention have a certain number of pharmacological properties which all converge on the correction of the effects on the tissue of ischaemia.

I. At the cardiac level:

(a) The compositions according to the invention considerably and significantly increase the survival time of the myocardium by delaying the appearance of irreversible ischaemic lesions.

The technique used is that recommended by Thomasset. It consists in measuring the survival time of an organ by measuring its impedance, which reflects the ionic exchanges through the membrane. In accordance with the technique used, the impedance of the isolated heart of a dog placed in a survival liquid was evaluated. When the hearts came from untreated animals, the average survival time was 32 minutes. When the animals had been treated previously with a dosage of 2.5 mg/kg administered intravenously before the organ was removed, the survival time increased to 49 minutes.

That increase in the survival time is caused by a slowing down of the cross-membrane ionic exchanges of sodium and potassium responsible for the appearance of an intracellular oedema, warning sign of the death of an organ.

(b) The compositions according to the invention correct the disturbances of the cellular metabolism of energy.

In animals, when an area has become ischaemic, an energy debt appears transitorily because of satisfaction of the accumulated needs of the organ for fighting the ischaemia. Ischaemia induced by injecting rats with vasopressin therefore brings about an increase in the energy metabolism of the heat. If the animals have been treated previously with a dosage corresponding to 2 mg/5 kg i.v. of 1-(2,3,4-trimethoxybenzyl)piperazine dihydrochloride for 5 consecutive days, that myocardial energy deficit is partially eliminated.

(c) The compositions according to the invention restore the energy potential of the myocardial cell.

In rats, the injection of vasopressin induces a breakdown of the adenosine triphosphoric acid content, a form of energy storage. In contrast, by previously treating the rats for 4 days with a dosage of 2 mg/5 kg administered orally and then on the fifth day with 2 mg/5 kg administered intravenously, the effects of vasopressin are eliminated. The adenosine triphosphoric acid concentrations return to a level identical to that found in the controls.

II. At the cerebral level the compositions according to the invention combat the disturbances of the electroencephalographic trace related to cerebral ischaemia.

Cerebral ischaemia can be brought about in rabbits by clamping the arterial vessels at their aortic origin. This causes the appearance of an electrical silence.

To verify the anti-ischaemic effects of the compositions according to the invention, solutions of 1-(2,3,4-trimethoxybenzyl)piperazine at dosages corresponding to 0.625 and 1.25 mg/kg were injected intravenously into groups of rabbits immediately before the clamping. The compositions according to the invention increase the resistance of the brain to anoxia. The disturbances in the electro-encephalographic trace appeared after a latency period of from 45 to 56 seconds, whereas in the control animals these disturbances appeared as early as 36 seconds.

accelerate the post-ischaemic recovery time. After the clamps had been removed, a relatively rapid return of global electrical activity (from 13 to 16 seconds in the treated animals compared with 30 seconds for the control animals) and a very rapid return of cortical reactivity (from 5 to 6 seconds for the treated animals compared with 33 seconds for the control animals) was observed.

restore the energy potential of the cerebral cell when it has been broken down during insufficient irrigation caused by slow injection of vasopressin.

III. At the retina:

The compositions according to the invention combat all ischaemic conditions of the chorio-retinal cells.

(B) Results of the clinical experiments using the compositions according to the invention in the treatment of energy deficits related to ischaemia.

I. Evaluation of the dose/activity relationship in chronic angina pectoris

Pharmacological and clinical appraisals of 1-(2,3,4-trimethoxybenzyl)piperazine have shown that this product protects homeostasis by restoring the energy activity of the cell exposed to hypoxia and by controlling the cross-membrane ionic flows of sodium and potassium. Its use in the treatment of angina pectoris is therefore justified because of its anti-anoxic metabolic properties.

The aim of that work was to study the effects of several dosages of the (trimethoxybenzyl)piperazine in patients suffering from angina, in comparision with a placebo period.

The therapeutic effectiveness was checked, in a single blind study, by statistical analysis of:
the number of attacks of angina,
the consumption of trinitrine,
the parameters of the effort tests.

Protocol

1. Choice of patients
   patients of both sexes
   suffering from chronic angina pectoris developed over at least 6 months, and
   having a positive effort test, this positive character being demonstrated by
   anginal pain,
   associated with a depression of segment S-T $\geq 1.5$ mV., caused by lesions.

2. Experimental Methods
   (a) The therapeutic sequences were preceded by a period of withdrawal that was sufficient for the patients following an anti-anginal therapy and comprising:
   a placebo period of 8 days,
   then four periods of therapy, each of 15 days, with:

| (trimethoxybenzyl)piperazine: | 10 mg/day × 15 days |
| | 20 mg/day × 15 days |
| | 40 mg/day × 15 days |
| | 60 mg/day × 15 days |

The patient was his own control.

The placebo and the different dosages of the (trimethoxybenzyl)piperazine were administered in identical manner, at the rate of three doses daily.

The (trimethoxybenzyl)piperazine tablets and the placebo tablets were identical and could not be distinguished by the patient.

(b) Criteria for assessment of the therapeutic activity: These were:
the number of spontaneous or provoked attacks of anginal pain noted by the patient within a week, assessed
before the test,
at the end of the placebo period, and
at the end of each therapeutic sequence with the (trimethoxybenzyl)piperazine,
the parameters of the maximum effort test carried out (product of the number of watts at the maximum level multiplied by the effort time at that level):
the intensity of pain triggered by the effort, rated as follows:

| 0 | no pain |
| 0.5 | minimum anginal pain |
| 1 | clear anginal pain |
| 2 | intense anginal pain |
| 3 | very intense anginal pain. | the severity of the depression, caused by lesions, of the S-T segment, rated in millivolts.

These parameters were always noted at the maximum effort of each test carried out on an ergometric bicycle having an electromagnetic brake by a clinician who did not know the stage of the therapy, at the following times:
at the end of the placebo period, and
at the end of each therapeutic sequence.

(c) Criteria for assessing the tolerance to the therapeutic sequences: This involved:
observation of the
digestive,
neuro-sensory, and
mucocutaneous organs,
assessment of the variations in the cardiac frequency and in the arterial blood pressure at rest,
the parameters of the effort test;
measuring the cardiac frequency and the systolic arterial blood pressure at maximum effort, and
calculating the product of the cardiac frequency multiplied by the systolic arterial blood pressure, or the systolic tension time which reflects the oxygen consumption of the myocardium.

3. Method of statistical analysis of the results

The criteria for assessing the activity and the criteria listed for assessing the tolerance were all analysed according to the same method, after their distribution had been verified.
analysis of variance to one or two factors with orthogonal factorisation.

Results

1. The population studied comprised 27 patients aged from 43 to 79 years with an average age of 60 years, of which 25 were men aged from 43 to 79 years with an average age of 60 years and 2 were women of 56 and 65 years.

2. Therapeutic activity: From the outset of the study a major difficulty was encountered: the clinical ineffectiveness of the 10 mg/day therapeutic sequence. Preceded by the placebo period of 8 days, that sequence of 10 mg/day for 15 days resulted in 3 weeks of treatment without result. It was not possible to maintain that sequence in all the patients and it could be continued only in 14 cases.

The statistical analysis (analysis of variance to one factor with orthogonal factorisation) confirmed the ineffectiveness of 10 mg/24 hours on the parameters studied.

That analysis confirmed the lack of clinical effectiveness of that dosage:
conflict between the parameters.
low significance of the parameters that varied, and
no significant action on the variations of the S-T, therefore, on the coronary reserve.

It was possible to analyse the results in a much more vigorous manner on the sequences:

| before placebo treatment, and (trimethoxybenzyl)piperazine | 20 mg/24 hours 40 mg/24 hours 60 mg/24 hours |
|---|---|

(a) Number of attacks of agina per week:

| Before Treatment | PLACEBO | 20 mg/day | 40 mg/day | 60 mg/day |
|---|---|---|---|---|
| 2.18 | 2.69 | 1.83 | 0.77 | 0.77 |

Orthogonal factorisation, with 1 and 84 degrees of freedom, showed that:
with the placebo, there was a slight increase in the number of attacks of angina per week (F=4.6429 P<0.05),
the (trimethoxybenzyl)piperazine, from 20 mg/24 hours, reduced in a highly significant manner (P<*0.001) the number of attacks of pain per week, and that
this action was at a maximum at the dosage of 40 mg/24 hours (P<*0.001) in a highly significant manner, without the appearance of a significant difference between 40 and 60 mg/24 hours.

*Although the sign "<" did not appear in the French text it is assumed that it was intended.

(b) Trinitrine consumption per week:

| Before Treatment | PLACEBO | 20 mg/day | 40 mg/day | 60 mg/day |
|---|---|---|---|---|
| 1.36 | 1.91 | 0.97 | 0.47 | 0.48 |

Orthogonal factorisation showed results perfectly consistent with the number of attacks of angina:
highly significant activity of (trimethoxybenzyl) piperazine from 20 mg/24 hours (P<0.001)
maximum activity at 40 mg/24 hours, in a significant manner (P<0.001), without a significant difference between 40 and 60 mg/24 hours (c) Parameters of the effort test:
1. Maximum effort capacity (product of the number of watts multiplied by the time at the maximum effort level.

| PLACEBO | 20 mg/day | 40 mg/day | 60 mg/day |
|---|---|---|---|
| 177.83 | 223.91 | 210.43 | 216.96 |

Orthogonal factorisation showed that, whatever the therapeutic sequence considered, the activity of the (trimethoxybenzyl)piperazine was significant. The variation of this parameter in the course of short therapeutic sequences illustrates very well the activity of the product.

2. Intensity of anginal pain at maximum effort

| PLACEBO | 20 mg/day | 40 mg/day | 60 mg/day |
|---|---|---|---|
| 1.48 | 0.80 | 0.43 | 0.28 |

Orthogonal factorisation showed that:
the activity of the (trimethoxybenzyl)piperazine was highly significant (P<0.001) from 20 mg/day
that activity was at a maximum at 40 mg/day, in a highly significant manner, P<0.001, without a significant difference between 40 and 60 mg/day.

3. Under-displacement, caused by lesions, of the S-T segment at maximum effort

| PLACEBO | 20 mg/day | 40 mg/day | 60 mg/day |
|---|---|---|---|
| 2.37 | 2 | 1.67 | 1.48 |

Orthogonal factorisation provided results identical with those obtained with the preceding parameters:
highly significant activity, P<0.001, from 20 mg/day.
minimum activity, highly significant between 40 and 60 mg/24 hours.

Conclusion on the parameters of activity of the (trimethoxybenzyl)piperazine:

This study shows that in cases of chronic coronary insufficiency developed over at least 6 months, the developed character being shown by a positive effort test (anginal pain and under-displacement, caused by lesions, of the S-T superior or equal to 1.5 mV), the compositions according to the invention, in comparison with a placebo, are
not effective at 10 mg/24 hours
and show a highly significant therapeutic effectiveness (P<0.001) from 20 mg/day on:
the number of attacks of anginal pain per week.
the trinitrine consumption per week, and
the parameters of the effort tests especially on the depression, caused by lesions, of the S-T, evidence of the coronary reserve, which effectiveness attains a maximum at the dosage of 40 mg/day.

There is therefore a threshold beyond which the antiischaemic activity appears.

3. Tolerance:
No problems occurred; neither
digestive disorders, nor
changes in appetite, nor
changes in sleeping or wakefulness,
mucocutaneous disorders, were observed.

General Conclusion

This study on 27 patients suffering from chronic angina pectoris, with positive effort test, (anginal pain and depression, caused by lesions, of the S-T, 1.5 mV) in a single blind study against a placebo, has shown that in the experimental conditions of the test:

the dosage of 10 mg of the (trimethoxybenzyl)piperazine daily has an insufficient therapeutic activity (the activity did not reach a degree of statistical significance), from the dosage of 20 mg of the (trimethoxybenzyl)piperazine daily the therapeutic activity becomes highly significant (P<0.001), and at the dosage of 40 mg of the (trimethoxybenzyl)piperazine daily the therapeutic activity is at a maximum in a highly significant manner (P<0.001), with a satisfactory tolerance.

II. At the retina:

The aim of the following study was to demonstrate the activity of the (trimethoxybenzyl)piperazine in the form of tablets of 20 mg on structures especially sensitive to ischaemia—the retina and the papilla.

1. The patients:

12 patients (three women and nine men) took part in the study. They were patients hospitalised as emergency cases of acute retinal, papillary or choroidal ischaemia of a type secondary or post-contusive to a vascular attack. The average age of that population was 39.8±14.4 years.

There were seven unilateral contusions of the eyeball and five ischaemic attacks of the retina or the optic nerve: occlusion of the central artery of the retina, of the central vein of the retina, vascular pseudo-papillitis, obliteration of a cilioretinal artery.

2. Methods of treatment:

Treatment using the compositions according to the invention was started within a period dating from the day of diagnosis itself to 2 weeks after diagnosis. The treatment was the (trimethoxybenzyl)piperazine, in injectable form, each ampoule containing 20 mg, at a dosage of one or two ampoules daily, that is to say from 20 to 40 mg, for from 7 to 10 days by continuous perfusion or direct intravenous injection and prescribed as the only therapy. The average length of treatment was 9 days.

3. Criteria of activity:

For all the patients the examination was the same and comprised:

(a) an ananmestic enquiry to find out:
the subjective visual signs (decrease in acuity, scotoma, metamorphopsia, myiodesopsia);
the ocular and general, personal and family history;
(b) an ocular examination comprising:
assessment of the visual function,
near and distant acuity,
central visual field (static) with Friedman analyser,
peripheral visual field (kinetic) with Goldmann apparatus,
examination by slit lamp to evaluate the transparency of the ocular media;
measure of the ocular tonus,
the back of the eye and biomicroscopy which shows clearly the condition of the macula, the pigment epithelium and the retinal vessels,
retinography in white and anerythric (without red radiation) light,
angiography using fluorescein, which analyses retinal circulation times, morphological anomalies, disorders in vascular permeability, capillary occlusions and plasmatic extravasations;
(c) a general examination seeking an extra-ocular cause for the opthalmic disorders (arterial hypertension, stenoses of the neck vessels).

4. Criteria of tolerance:

The tolerance to the (trimethoxybenzyl)piperazine 20 mg was observed on three levels:

at a local level by a careful examination for any sign of irritation or inflammation at the point of injection;

at a clinical level by a daily examination for any cardio-vascular, neurological, renal, digestive or cutaneous sign;

at an ocular level using the above-mentioned detailed examination.

Results (1) Overall results:

The overall results were divided into four categories:
very good results: recovery ad integrum;
good results: very clear improvement in more than four parameters;
average results: improvement in more than two parameters;
no results: absence of improvement.

| RESULTS | No. | % | |
|---|---|---|---|
| very good | 1 | 8.3 | |
| good | 7 | 58.3 | } 66.6 |
| average | 3 | 25 | |
| none | 1 | 8.3 | |

In total, in 12 patients, the (trimethoxybenzyl)piperazine at the dosage of 20 mg brought about 8 very good results, that is to say in 66.6% of the cases.

(2) Results as a function of pathology:

(a) Contusions of the eyeball in 7 patients:

5 good results were obtained, and 2 average results. Visual acuity was most sensitive to the therapy since it was very clearly improved in 5 cases, two patients having a progression of acuity from 4 and 5 tenths to 10 to 12 tenths, respectively. The appearance of the retina corroborated this improvement perfectly. The speed of recovery was remarkable, less than 6 days in 6 cases out of 7.

(b) Ischaemic disorders of the retina and of the papilla present in 5 patients.

3 good results were noted, of which one was a complete recovery, 1 average result, and 1 failure.

The back of the eye was completely or clearly better in 4 of the five patients. The single failure was noted in an extremely severe pathological disorder that was not very accessible to the therapy: pseudo-papillitis of an atheromatous origin.

(3) Results as a function of the functional and retinoangiographic examinations.

(a) Visual acuity was very sensitive to the treatment:

In 10 of the 12 patients, there was a very clear improvement which appeared from the 3rd day of treatment in 7 of the twelve patients. Acuity returned to normal at the end of treatment in 5 cases out of 12, that is to say in 41.6% of the patients.

(b) The central visual field was altered in 11 patients, Nine of them saw an improvement which in 6 patients appeared also from the 3rd day of treatment.

(c) The peripheral visual field, which was altered in 5 of the patients, improved in 4 of them.

(d) Retinography showed an improvement in the lesions of the posterior pole of the eye in 11 cases out of 12, that is to say in 92% of the patients, in the form of:

disappearance or regression of the ischaemic oedema and of the retinal haemorrhages, and disappearance of the papillary oedema in one of the 2 patients suffering from this.

These results appeared also at an early date, between the 2nd and the 4th day of treatment in 7 out of the 11 patients, that is to say for 64% of them.

(e) Angiofluorography showed a morphological appearance that had virtually returned to normal in 8 cases out of 9; furthermore, the retinal circulation time improved in 3 cases out of 5.

4. Tolerance.

Both at the local level as well as at the general or ocular level, the (trimethoxybenzyl)piperazine at 20 mg provoked no incident. This perfect tolerance is an additional favourable argument for patients who are often undergoing several treatments.

Conclusion

In the form of an injectable solution containing 20 mg the (trimethoxybenzyl)piperazine is a novel anti-ischaemic therapy having an original mode of action. In fact, it is aimed at directly protecting the cell from the consequences of ischaemia by controlling the cellular cross-membrane ionic flows which are disturbed in the course of ischaemia.

The pharmaco-clinical study undertaken in 12 patients suffering from acute retinal or papillary ischaemia or from ocular contusions has revealed the benefits that may be expected. Indeed, the visual acuity, the back of the eye, the visual field and angiofluorography have amply demonstrated the therapeutic effectiveness of the (trimethoxybenzyl) piperazine at an average dosage of from 20 to 40 mg/day: 67% of the patients thus benefitted from a relatively early restoration of the visual functions, related to a favourable anatomical development.

III. In otolgy:

A double blind study was carried out in order to verify the results obtained in a previous study on two indications, Ménière's vertigo and vascular vertigo, by comparing the effectiveness of the (trimethoxybenzyl) piperazine at 20 mg with that of a major product as reference, the activity of which product on symptoms of vertigo is recognised. The dosage was two tablets daily for 3 months.

1. Material and method:

This study was carried out on 40 cases involving 17 men and 23 women aged from 18 to 72 years (average age: 46 years). The 20 subjects suffering from Meniere's disease were clearly younger (average age 33 years) than the other 20 subjects suffering from vascular vertigo (average age 59.5 years).

The treatment considered as a basal treatment consisted of prescribing, without any associated therapy, (trimethoxybenzyl)piperazine at a rate of 40 mg/day, or the reference product at a rate of 24 mg/day, in 2 daily doses for 3 months.

The distribution of the two products was done by drawing lots for each of the two indications involved. The units of treatment were given to the patient according to his order of entry into the study.

Clinical and para-clinical criteria based on the symptoms presented made it possible firstly to assess the condition of the patients before treatment and, in the same manner, to compare the pathological condition of the two therapeutic groups in order to verify the intrinsic activity of the (trimethoxybenzyl)piperazine at 20 mg, and of the reference product, and then to compare the results obtained with the one and the other product.

The criteria were the following:

attacks of vertigo: the length, frequency and intensity of the attacks of vertigo were rated using a score of seriousness of from 3: very severe disorder, to 0: absence or disappearance of the disorder.

vestibular examinations: Barany's caloric test and pendular tests using electronystagmographic recording.

tinnitus: The intensity, frequency and length were rated using a score of seriousness of from 3: very intense disorder, to 0: absence or disappearance of the disorder.

effect on hearing: assessed subjectively.

audiometry: assessment of the loss in decibels at both ears.

Before assessing the results, the homogeneity of the two populations was investigated.

The two therapeutic groups were revealed to be comparable with regard to their population (number of patients, age, sex), the diagnosis made (equal number of Ménière's vertigo and vascular vertigo in each group), the duration of the disorders (from 6 months to 5 years) and the symptoms presented.

The application of different statistical tests to the above-described parameters resulted in the conclusion that there was no statistically significant difference between the two groups.

Finally, there was also a homogeneity between the two diagnostic sub-groups: the pathological condition presented was comparable in the patients suffering either from Ménière's vertigo or from vascular vertigo in both the (trimethoxybenzyl)piperazine 20 mg group and in the reference group.

2. Results:

2.1.: Therapeutic activity of the two products studied.

The results obtained on the symptoms presented were as follows:

With the (trimethoxybenzyl)piperazine 20 mg tablets, the attacks of vertigo disappeared, or decreased very clearly in intensity and frequency, in 79% of the cases, the score moving from 3 to 1.05 ($P<0.001$).

The buzzing in the ear disappeared, or improved very clearly, permanent buzzing becoming intermittent or of a lesser intensity in 55.5% of the cases, resulting in better auditory comfort in the same proportions, the score moving from 2 to 0.722 ($P<0.001$).

The vestibular tests showed a return to normal, or gave a better response or a better trace, in the caloric test in 69% of the cases, and in 74% of the cases in the pendular test with electronystagmography.

The audiometric curve improved from 5 to 10 dB in 37% of the cases.

2.2.: Inter-product comparison:

Statistical comparison, between the two therapeutic groups, of the benefits obtained after treatment was carried out on several levels:

comparison of the symptoms

Comparable activity of the 2 products:
on the attacks of vertigo, Mann and Whitney test(NS)
on the vestibular tests, chi-squared test(NS)

Superior activity of the (trimethoxybenzyl)piperazine at 20 mg:
on buzzing in the ears, Mann and Whitney test ($P<0.02$)

comparison with previous treatments

Comparison of the results obtained with the (trimethoxybenzyl)piperazine at 20 mg and with the reference product in relation to different treatments administered previously revealed a difference in favour of the (trimethoxybenzyl)piperazine at 20 mg.

the latter was shown to be superior in 70% of the cases.

the reference product was shown to be superior in 45% of the cases.

comparison of the quality of the improvement

Good and excellent results were obtained in 75% of the cases with the (trimethoxybenzyl)piperazine at 20 mg and in 40% of the cases with the reference product.

The difference found between the number of excellent and good results was significant and favoured the (trimethoxybenzyl)piperazine at 20 mg, chi-squared test=5.02 ($P<0.02$).

comparison as a function of the nosological diagnosis.

The difference in activity was principally in the vascular vertigo where the excellent and good results reached 80% with the (trimethoxybenzyl)piperazine at 20 mg in contrast to 20% with the reference product ($P<0.01$), whereas the results obtained in Ménière's vertigo were comparable: 70% with the (trimethoxybenzyl)piperazine at 20 mg and 60% with the reference product.

The clinical tolerance of the (trimethoxybenzyl)piperazine at 20 mg and the reference product was excellent in all points.

In normal conditions of use, no harmful effect due to the treatment was revealed in the patients; the absence of side-effects on the cardio-vascular apparatus, the central nervous system and the digestive system deserves to be emphasised.

Furthermore, no allergic reaction was noted.

IV: At the coronary level:

The aim of the controlled double blind crossover study was to evaluate the therapeutic interest of the compositions according to the invention compared with a major anti-anginal medicament, perhexiline maleate, as reference.

1. The patients:

The study was carried out initially on 36 coronary patients having an average age of 45.7±2.7 years, who were hospitalised in a cardiac rehabilitation centre. The patients were assigned at random to two groups, the groups being comparable with regard to the localisation of the infarct and the early complications of the infarct.

2. The method:

In each group the treatment lasted one month, from the end of the first to the end of the second month after the infarct, and was administered at a rate of 40 mg/day of the (trimethoxybenzyl)piperazine in tablets of 20 mg and 400 mg/day of perhexiline maleate in two daily doses taken at mealtimes.

The patients underwent 3 effort tests on an ergometric bicycle:

the first effort test(T1), carried out just before the beginning of the treatment (that is to say, on average, 30 days after the infarct), was continued until a maximum theoretical frequency (MTF) was obtained. Definition of MTF: 220—age.

the second and third effort tests(T2 and T3), carried out at the middle and end of the treatment (on the 45th and 60th day after the infarct) respectively, were continued until a cardiac frequency equal to the maximum theoretical frequency was obtained, except when the patient stopped earlier owing to exhaustion, ischaemic disorders and maladjustment to effort.

The electrocardiographic recordings and the measurements of arterial blood pressure carried out during the treatment were the subject of statistical analysis (Student test for paired series).

3. Criteria of activity:

During those ergometric tests, the activity of the (trimethoxybenzyl)piperazine and of the reference product was assessed on two criteria:

on the one hand, study of the development of the coronary reserve to effort, that is to say study of the adjustment of the coronary network during an increased demand for oxygen during effort. The coronary reserve may be defined as being the threshold of appearance of an under-displacement of the S-T segment during effort, and is expressed either as a percentage of the maximum theoretical frequency (MTF) or as a function of the systolic tension time or STT (product of the systolic arterial blood pressure multiplied by the cardiac frequency) which is itself parallel to the oxygen consumption.

The subjects involved were those whose electrical trace was modified at T1, in other words those whose coronary reserve was $\leq 70\%$ of the MTF before treatment. The sample was therefore restricted to the most seriously ill patients.

on the other hand, study of the development of the adjustment of the cardio-circulatory system during effort, that is to say study of the diminution in the STT, thus in the work of the heart, for the same level of effort expressed in watts. Only subjects capable of producing a level of work sufficient to be significant, that is to say 80 W at T1, were retained for this test.

Those criteria having been studied at times (T1, T2, T3) of the experiment, two comparisons were then carried out:

before/during the treatment($\Delta$T2/T1)
before/at the end of the treatment($\Delta$T3/T1).

4. Results after treatment with (trimethoxybenzyl)piperazine at 20 mg with regard to the coronary reserve, patients showing no significant electrical modification at the first sub-maximum effort test(T1) were eliminated, that is to say 10 of the 17 patients in the 20 mg (trimethoxybenzyl)piperazine group. The observations therefore related to 6 patients between the first and the second test and to 7 patients between the first and the third test, one of the 7 patients not having undergone the test at T2.

Analysis of the data recorded during these tests revealed a significant increase of 18% in the coronary reserve expressed as a percentage of the maximum theoretical frequency. This improvement noticed from T2, on average 18 days after the beginning of the treatment, continued at T3, on average 32 days after the beginning of the treatment.

If the results are expressed as a function of STT, the improvement in the coronary reserve is 19% at the second test(T2) and 22% at the third test(T3). Taking into account the uncertainties related to the determination of the STT, the increase of the latter is not significant, but it agrees with the significant improvement in the coronary reserve expressed as a percentage of the maximum theoretical frequency.

With regard to the adjustment to effort, the number of observations retained after having removed the patients unable to provide an effort of 80 watts in the first test, was 12 between T1 and T2 and 11 between T1 and T3.

A significant diminution in the average systolic arterial blood pressure at effort was observed, which caused a diminution in the oxygen consumption for the same level of effort.

It therefore appears that during effort the (trimethoxybenzyl)piperazine permits a saving in the oxygen consumption, without modifying the cardiac effort output, the myocardial contractility or the venous return.

It may therefore be considered that the (trimethoxybenzyl)piperazine is without risk in cardiac insufficiency.

comparison of the (trimethoxybenzyl)piperazine at 20 mg with perhexiline maleate.

In the cases involved and at two test times, the improvement in the coronary reserve obtained with the (trimethoxybenzyl)piperazine at 20 mg was significantly greater than that obtained with the major antianginal medicament used as reference.

With regard to the circulatory adjustment to effort, analysis of the data did not reveal any significant difference between the results obtained at the two test times with the two medicaments, their activity on this criterion therefore being comparable.

It appeared however, that, in contrast to the reference product, the (trimethoxybenzyl)piperazine at 20 mg permitted a significant drop in the systolic arterial blood pressure at effort, whereas it did not alter the arterial blood pressure at rest.

What we claim is:

1. A method for treating ischaemia in a patient which comprises administering to said patient a daily oral amount of a composition which comprises 20 to 80 mg of 1-(2,3,4-trimethoxybenzyl)-piperazine dihydrochloride and a pharmaceutically acceptable disintegrating agent.

2. A method according to claim 1 wherein the unit dose administered is 20 mg.

3. A method for treating ischaemia in a patient which comprises administering to said patient a daily oral amount of a composition which comprises 20 to 80 mg of a compound selected from 1-(2,3,4-trimethoxybenzyl)-piperazine and a pharmaceutically acceptable salt thereof and a pharmaceutically acceptable disintegrating agent.

4. A pharmaceutical composition for treating ischaemia which comprises 20 to 80 mg of 1-(2,3,4-trimethoxybenzyl)-piperazine or a pharmaceutically acceptable salt thereof and a pharmaceutically acceptable disintegrating agent selected from mannitol and carboxymethyl starch.

5. A composition of claim 4 wherein the active ingredient is 1-(2,3,4-trimethoxybenzyl)-piperazine dihydrochloride.

6. A composition of claim 5 wherein the composition comprises at least 20 mg of 1-(2,3,4-trimethoxybenzyl)-piperazine dihydrochloride.

* * * * *